(12) United States Patent
Mohit et al.

(10) Patent No.: US 9,730,767 B2
(45) Date of Patent: Aug. 15, 2017

(54) FINGER MOUNTABLE DENTAL HAND PIECE DEVICE

(71) Applicant: Kumar Khandelwal Mohit, Jharkhand (IN)

(72) Inventors: Kumar Khandelwal Mohit, Hazaribagh (IN); A. R. Vivekananda Pai, Mangalore (IN); Sarvesh Kumar Mishra, Gorakhpur (IN); Ishita Gupta, Bhopal (IN)

(73) Assignee: Kumar Khandelwal Mohit, Hazaribag, Jharkhand (IN)

( * ) Notice: Subject to any disclaimer, the term of this patent is extended or adjusted under 35 U.S.C. 154(b) by 0 days.

(21) Appl. No.: 14/916,596

(22) PCT Filed: Sep. 2, 2014

(86) PCT No.: PCT/IN2014/000571
§ 371 (c)(1),
(2) Date: Mar. 4, 2016

(87) PCT Pub. No.: WO2015/033352
PCT Pub. Date: Mar. 12, 2015

(65) Prior Publication Data
US 2016/0213446 A1 Jul. 28, 2016

(30) Foreign Application Priority Data
Sep. 4, 2013 (IN) .......................... 3972/CHE/2013

(51) Int. Cl.
*A61C 1/18* (2006.01)
*A61C 1/05* (2006.01)
(Continued)

(52) U.S. Cl.
CPC ................ *A61C 1/188* (2013.01); *A61C 1/05* (2013.01); *A61C 1/052* (2013.01); *A61C 1/12* (2013.01); *A61C 3/02* (2013.01); *A61C 19/006* (2013.01)

(58) Field of Classification Search
CPC .. A61C 1/05; A61C 1/052; A61C 1/12; A61C 3/002; A61C 19/006; A61C 19/004; A61C 1/18; A61C 1/188
See application file for complete search history.

(56) References Cited

U.S. PATENT DOCUMENTS

| 745,722 A | * | 12/1903 | Freeman .................. A61C 1/12 |
| | | | 279/77 |
| 1,163,866 A | * | 12/1915 | Sexton ................ A61C 19/006 |
| | | | 131/258 |

(Continued)

FOREIGN PATENT DOCUMENTS

GB 847262 A * 9/1960 ............... A61C 1/05

*Primary Examiner* — Nicholas Lucchesi
*Assistant Examiner* — Shannel Wright
(74) *Attorney, Agent, or Firm* — Prakash Nama; Global IP Services, PLLC

(57) ABSTRACT

The present invention relates to a finger mountable flexible dental hand-piece device. In one embodiment the hand piece device comprises of: a head portion and a body portion, wherein the head portion and the body portion are engaged by a flexible joint to provide flexible movement for the head portion. The head portion defines a head enclosed in a head shell, where the head shell is accompanied by a first finger band which is stipulated on the top of the head shell. The body portion has a first end and a second end; the first end of the body portion is to engage with the head portion, wherein there is a second finger band which is stipulated on the top of the body portion.

4 Claims, 6 Drawing Sheets

(51) Int. Cl.
*A61C 1/12* (2006.01)
*A61C 3/02* (2006.01)
*A61C 19/00* (2006.01)

(56) References Cited

U.S. PATENT DOCUMENTS

| | | | | | |
|---|---|---|---|---|---|
| 2,591,183 | A | * | 4/1952 | Mintz | A61C 1/082 433/76 |
| 3,229,369 | A | * | 1/1966 | Hoffmeister | A61C 1/18 433/105 |
| 4,127,338 | A | * | 11/1978 | Laybourne | B43K 23/012 401/8 |
| 4,213,472 | A | * | 7/1980 | Gueret | A46B 5/04 132/320 |
| 4,341,518 | A | * | 7/1982 | Wallace | A61C 1/088 433/29 |
| 4,382,790 | A | * | 5/1983 | Loge | A61C 1/18 433/126 |
| 4,602,650 | A | * | 7/1986 | Pipkin | B05C 17/00 132/317 |
| 4,679,274 | A | * | 7/1987 | Friedman | A46B 5/04 15/167.1 |
| 5,163,600 | A | * | 11/1992 | Barbarich | B23K 3/03 219/229 |
| 5,308,238 | A | * | 5/1994 | Beach | A61C 1/00 433/108 |
| D362,163 | S | * | 9/1995 | George | D8/7 |
| 5,538,425 | A | * | 7/1996 | Reeves | A61C 1/05 433/126 |
| 5,557,805 | A | * | 9/1996 | Emerson | A61F 5/0118 2/158 |
| 5,604,952 | A | * | 2/1997 | Zeleznick | A46B 3/18 15/167.1 |
| 5,616,029 | A | * | 4/1997 | Suzuki | A61C 1/18 433/118 |
| 5,772,436 | A | * | 6/1998 | Matsui | A61C 1/088 433/126 |
| 5,902,107 | A | * | 5/1999 | Lowell | A61C 1/12 433/112 |
| 5,953,783 | A | * | 9/1999 | Hahn | A46B 9/04 15/167.1 |
| 5,971,757 | A | * | 10/1999 | Selzer | A61C 1/0076 433/126 |
| 6,106,287 | A | * | 8/2000 | Yates | A61C 1/0076 433/80 |
| 6,423,070 | B1 | * | 7/2002 | Zeppelin | A61B 17/1622 606/170 |
| 6,944,914 | B2 | * | 9/2005 | Tillim | A61B 17/2909 16/421 |
| 7,179,087 | B2 | * | 2/2007 | Kuhn | A61C 1/052 433/114 |
| 8,850,662 | B2 | * | 10/2014 | Gitman | A61B 17/3213 16/430 |
| 2002/0127512 | A1 | * | 9/2002 | Chen | A61C 1/07 433/119 |
| 2004/0229186 | A1 | * | 11/2004 | Slone | A61C 3/00 433/29 |
| 2004/0237261 | A1 | * | 12/2004 | Rouse | B43K 23/012 24/10 R |
| 2005/0282111 | A1 | * | 12/2005 | Ito | A61C 1/10 433/131 |
| 2006/0226032 | A1 | * | 10/2006 | Zalsman | A45C 11/00 206/63.5 |
| 2008/0004612 | A1 | * | 1/2008 | Schmid | A61B 1/24 606/13 |
| 2011/0306010 | A1 | * | 12/2011 | Chronister | A61C 1/08 433/112 |
| 2013/0203013 | A1 | * | 8/2013 | Taddeo | A61C 17/04 433/94 |
| 2013/0203014 | A1 | * | 8/2013 | Lieb | A61C 1/185 433/131 |
| 2014/0272786 | A1 | * | 9/2014 | Olsen | A61C 19/006 433/163 |

* cited by examiner

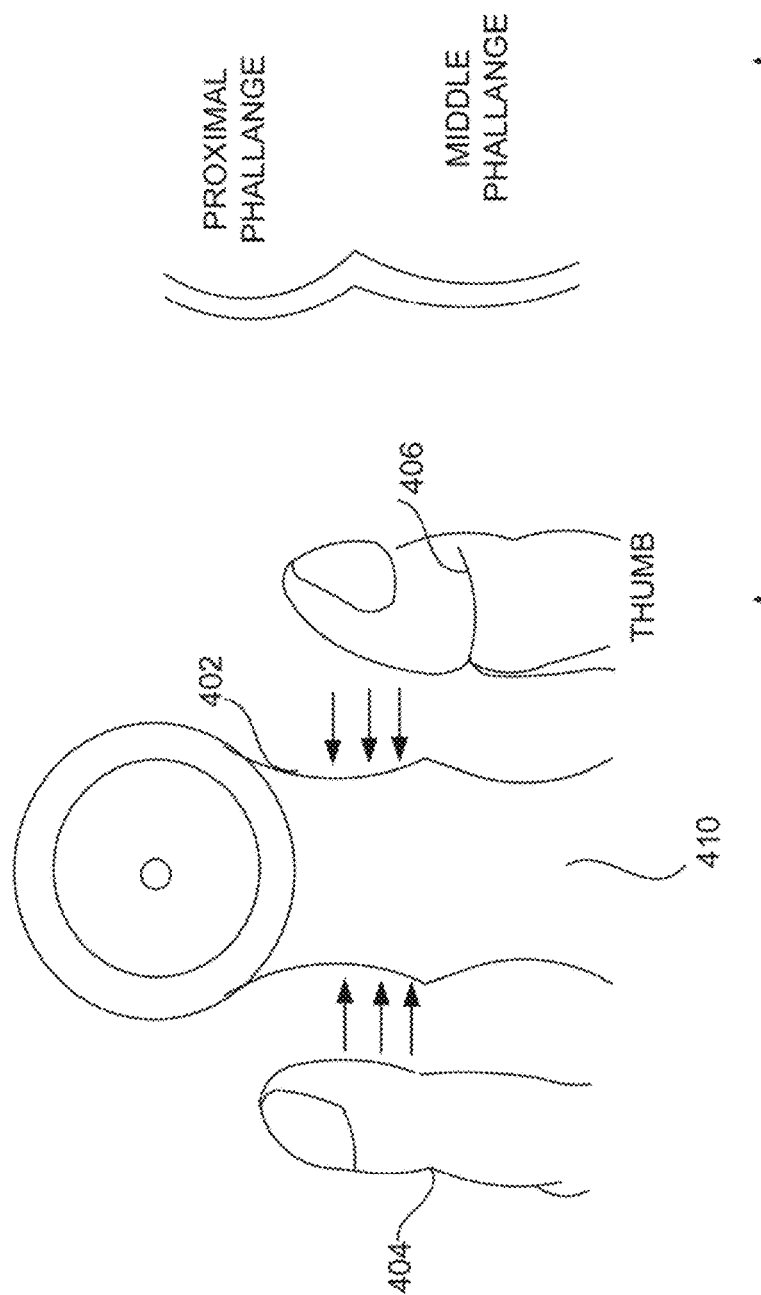

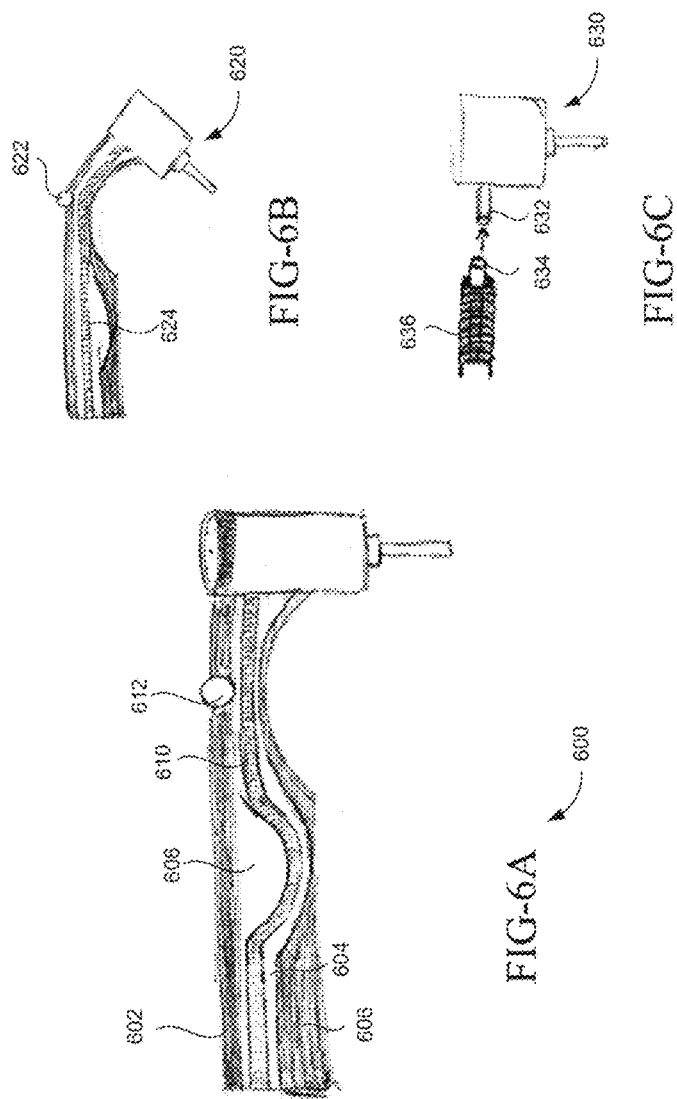

FINGER MOUNTABLE DENTAL HAND PIECE DEVICE

FIELD OF THE INVENTION

The present invention mainly relates to dental hand-piece and more particularly to the finger mountable flexible dental hand-piece device.

BACKGROUND OF THE INVENTION

A dental drill or dentist's drill or dental hand-piece is well known in the art which is a small, high-speed drill used by dentists during dental procedures, to bore through tooth enamel to clean and remove caries from the tooth surface so as to facilitate the insertion of a filling or crown, access opening in RCT (root canal treatment) and the likes.

Earlier, the dental hand-piece consisted of a head with a drill, neck and body which used a coiled wire spring to drive the drill. Later, they discovered a drill which was a motor drill powered by the spring action of a dock movement. Further, pneumatic (air-driven) drill was included in the dental hand piece which was powered by pedal bellows. Each of these additional developments were to increase the speed at which the drill operates.

The construction of the above mentioned dental hand-piece was complicated and involved large number of components to operate. This device was not flexible and therefore caused difficulties in reaching the less accessible carious areas in the oral cavity. Hence, to reduce the difficulties of this above mentioned dental hand-piece device, a dental hand-piece with simple construction powered by electricity, has been introduced to drive the drill.

Presently the dental hand-piece consists of a hand-piece body, head bearing, drive shaft, air motor, crown wheel gearing, bur or drill bit, air transport hose, motors, gears and the likes.

In addition to this, the dental hand-piece devices are made up of lightweight, hard plastics or metal alloys such as brass, titanium and the likes. The bur or drill bit is made of tungsten carbide, one of the hardest substances known. The tubing that connects the drill to the main power source is made of a flexible material, such as polymeric silicone or polyvinyl chloride (PVC) and other such materials. But still the problem exists, in the way of accessing the device.

Conventional dental hand-piece devices have a simple construction and the drills are turbine-powered which rotate at a speed ranging from 20,000 rpm to about 400,000 rpm (revolutions per minute). This generates a large amount of heat but is less irritating to the patients due to the use of appropriate coolant.

However, the above mentioned dental hand-piece device fails due to its lack of ability in reaching the less accessible areas of the oral cavity resulting in unnecessary cutting of tooth. Moreover, this device lacks stability which leads to the superfluous slipping of the hand-piece from operator's hands and cause damage to gingiva, palate, tongue and other soft tissues in the oral cavity. Besides, the presently used dental hand-piece device does not have a standard grip which leads to its reduced efficiency.

Therefore, there is a need in the art to introduce this innovative dental hand piece device with assured excellence that solves the above mentioned limitations.

SUMMARY OF THE INVENTION

An aspect of the present invention is to address at least the above-mentioned problems and/or disadvantages and to provide at least the advantages described below.

Accordingly, one aspect of the present invention relates to a finger mountable hand piece device, the device comprising of: a head portion and a body portion. Both head and the body portion are engaged by a flexible joint to provide flexible movement of the head portion. The head portion consists of a head enclosed in a head shell. To this head shell, is attached the first finger band which is stipulated on top of the head shell. The body portion consists of a first end and a second end, the first end engages with the head portion and it is attached to the second finger band which is stipulated on top of the body portion.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features, and advantages of certain exemplary embodiments of the present invention will be more apparent from the following description taken in conjunction with the accompanying drawings in which:

FIGS. 4 (a) and 4 (b) shows the top view of head of dental hand piece device and the fingers facing the two depression surfaces of the hand piece according to one embodiment of the present invention.

FIG. 5 (c) shows the cross section view of end part compartments of body portion of dental hand piece device according to one embodiment of the present invention.

FIG. 6(a) shows the longitudinal section view of the dental hand piece device with the flexible joint inactive according to one embodiment of the present invention.

FIG. 6(b) shows the longitudinal section view of the dental hand piece device with the flexible joint activated according to one embodiment of the present invention.

FIG. 6 (c) shows the body configuration of the pipe or tube and its attachment to the slot in the head of the dental hand piece device according to one embodiment of the present invention.

Figure 1:
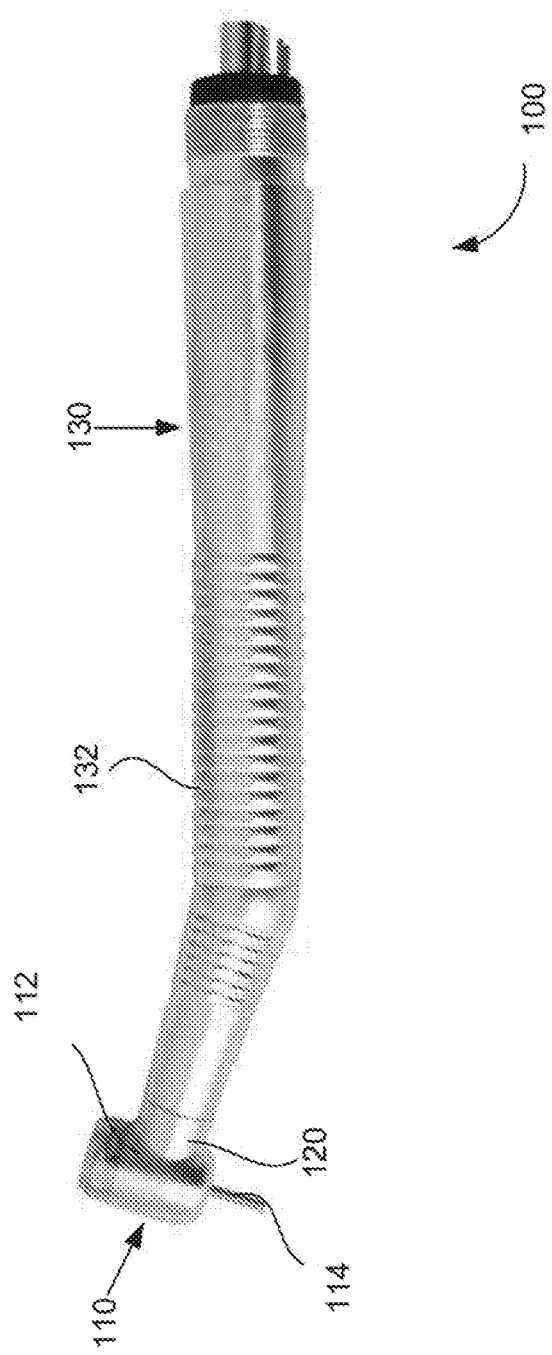
FIG. 1 shows the perspective view of a typical hand piece device.

Persons skilled in the art will appreciate that elements in the figures are illustrated for simplicity and clarity and may have not been drawn to scale. For example, the dimensions of some of the elements in the figure may be exaggerated relative to other elements in order to improve the understanding of various exemplary embodiments of the present disclosure.

Throughout the drawings, it should be noted that like reference numbers are used to depict the same or similar elements, features, and structures.

DETAILED DESCRIPTION OF THE INVENTION

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions are omitted for clarity and conciseness.

The terms and words used in the following description and claims are not limited to the bibliographical meanings, but are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents. It is to be understood that the singular forms "a," "an," and "the" include plural referents unless the context clearly dictates otherwise. Thus, for example, reference to "a component surface" includes reference to one or more of such surfaces. By the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide. FIGS. 1 to 6, discussed below, and the various embodiments used to describe the principles of the present disclosure in this patent document are by way of illustration only and should not be construed in any way that would limit the scope of the disclosure. Those skilled in the art will understand that the principles of the present disclosure may be implemented in any suitably arranged communication system. The terms used to describe various embodiments are exemplary. It should be understood that these are provided to merely aid in the understanding of the description, and that their use and definitions in no way limit the scope of the invention. Terms first, second, and so on, are used to differentiate between objects having the same terminology and are in no way intended to represent a chronological order, unless where explicitly stated otherwise. A set is defined as a non-empty set including at least one element.

FIG. 1 shows the perspective view of a typical hand piece device.

FIG. 1 shows the perspective view of the dental hand piece device (100) used for working in the oral cavity of human beings. The dental hand piece device (100) includes a head (110), neck (120) and body (130) thereof. Body portion (130) of the dental hand piece device (100) is joined to the head portion (110) with the assistance of elongated neck (120). The head (110) includes, head shell (112), bur/dental drill (114), and a turbine cartridge assembly (not shown). The body portion (130) of the dental hand piece consists of an upper end portion and a lower end portion having an outer wall with flutes (132) which provide a hand-gripping surface.

Figure 2:
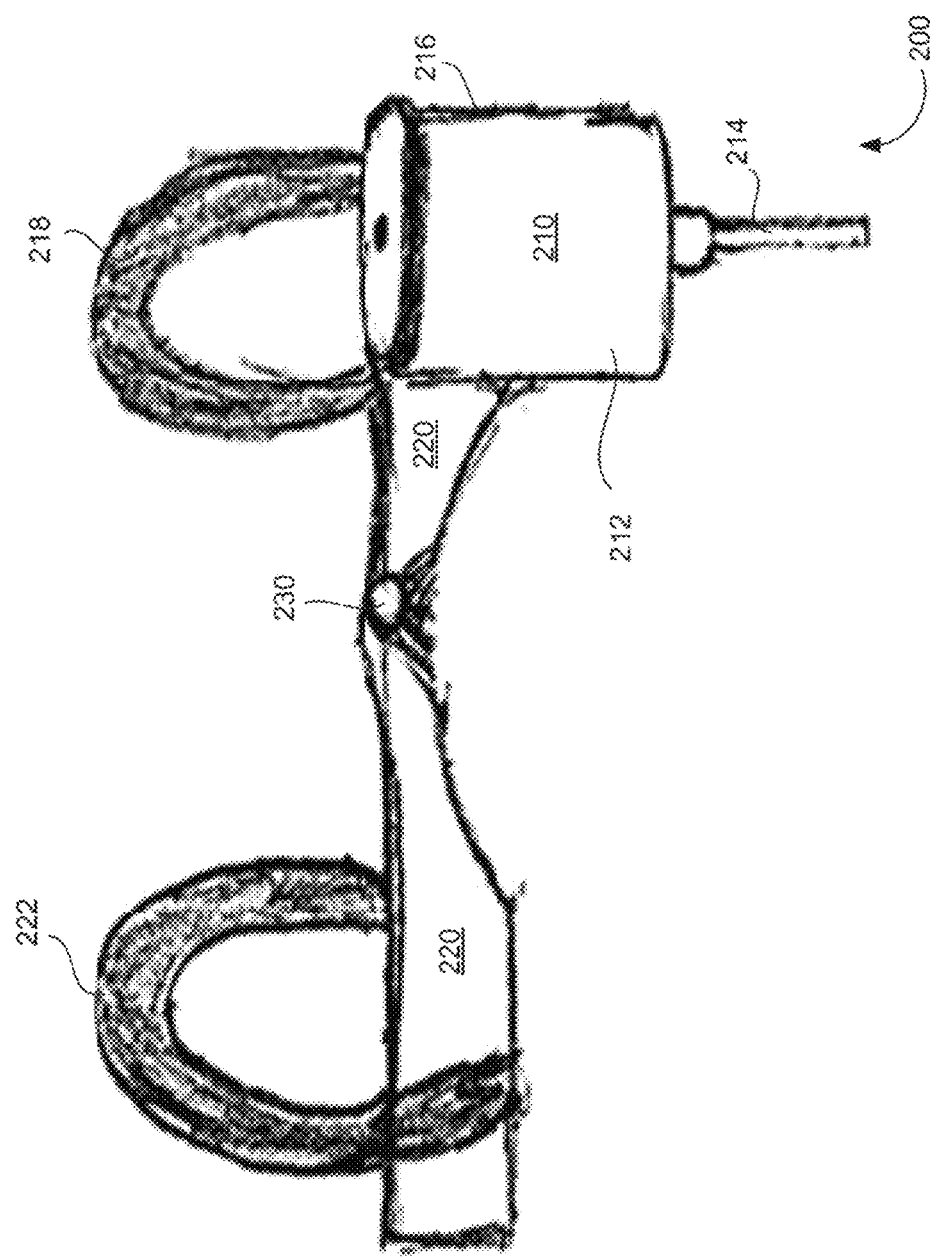
FIG. 2 shows the perspective view of shortened dental hand piece device with finger rings according to one embodiment of the present invention.

FIG. 2 shows perspective view of shortened dental hand piece with finger rings according to one embodiment of the present invention.

The FIG. 2 shows perspective view of shortened dental hand-piece device (200) to work in the oral cavity of human beings. It has a shortened body compared to other hand pieces. This shortened dental hand piece comprises of a head portion (210) and a body portion (220), where both the portions are joined by welding/bonding. The head portion (210) of the dental hand piece includes the head (212), which is enclosed by a head shell (216). The head (212) comprises of a small turbine with a central slot to accommodate the cutting unit of the instrument known as bur/dental drill (214). This dental burr/drill (214) is positioned at the centre of the head (212) of the head portion (210) of the shortened dental hand piece (200).

The body portion (220) of the dental hand piece (200) is elongated and extends up to the proximal end of the middle phalanx of the index finger which provides the additional accessibility in difficult areas of the oral cavity of patients. If the length of the body portion exceeds proximal to the proximal end of the middle phalanx, the mobility of the proximal inter-phalangeal joint will be hampered preventing the access in difficult areas in patient's mouth, that is otherwise easily provided due to the mobility of this proximal inter-phalangeal joint.

The shortened dental hand piece device (200) includes two or more adjustable finger rings. The head portion (210) of the dental hand piece includes one finger ring (218) on top of the head shell of the head to engage the distal phalanx of the index finger and the body portion of the dental hand piece includes the other finger ring (222) to engage the middle phalanx of the index finger, which provides control to the operator to reach the difficult areas comfortably. The finger rings used can be an adjustable metal finger ring or an elastic finger ring made of synthetic rubber or a finger strap. The dental hand piece device comprises of a hinge joint (230) in the body portion (220) that provides a flexible movement for the head portion (210). The hinge joint (230) lies just below the distal inter-phalangeal joint of the index finger to make the maximum use of the mobility of that joint while controlling the device.

Figure 3B:
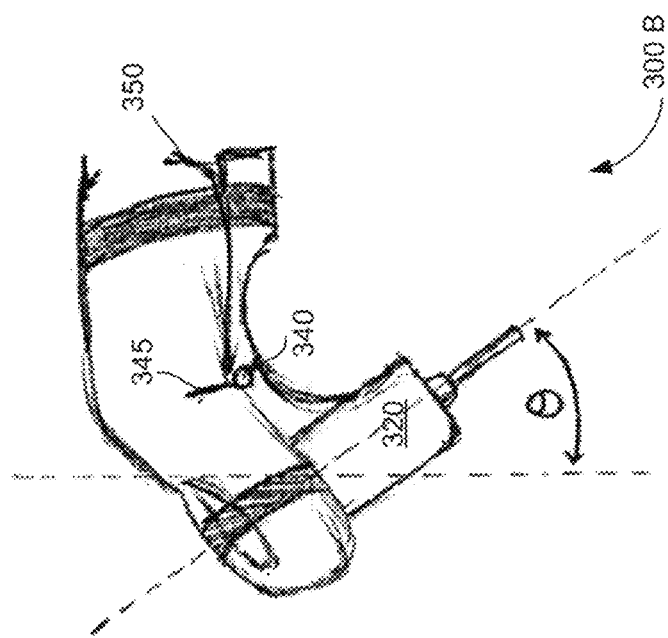
FIGS. 3(a) and 3(b) shows the perspective view of the dental hand piece device with the insertion of finger in the finger ring and the angle rotation of dental hand piece device according to one embodiment of the present invention.
Figure 3A:
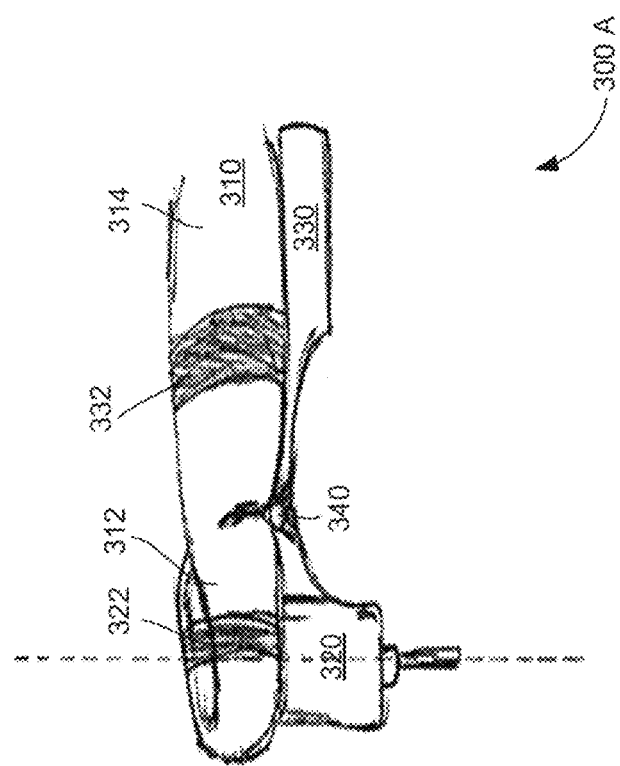

FIGS. 3(a) and 3(b) shows the perspective view of the dental hand piece with the insertion of finger in finger rings and the angle rotation of dental hand piece according to one embodiment of the present invention.

The FIG. 3(a) shows the perspective view of insertion of index finger (310) in the dental hand piece device (300a) and the position that the rings (322) and (332) will hold around the phalanx of index finger (310). The joint (340) as shown in figure defines the joining of the head portion (320) and the body portion (330) whose position coincides with the distal inter-phalangeal joint of the index finger. The head portion (320) and the body portion (330) of the dental hand piece device (300a) are joined with the help of metal slot (not shown) in head portion and polysilicon elastomeric pipe (not shown) in the body portion. It also provides a hand piece device design which is short in size and with a better control for the operator during function. It also allows the operator to access the difficult areas of mouth and surfaces of teeth with ease. This finger mounted dental hand piece device is so designed that it is firmly attached to the index finger (310) and together with head (320) and body portion (330) they work as a single unit. This prevents slipping of the hand piece, which otherwise may sometimes be experienced with the modified pen grasp.

The design of the invention is such that the back/top of the head portion (320) of hand piece is in an intimate contact with the ventral surface of the distal phalanx (312) of the index finger to provide better tactile sensitivity while cutting the tooth structure or removing decay or any work related to oral cavity. The proposed device is provided with a finger rest surface for index finger (310), and two depressions on both the sides for resting the thumb and the middle finger, thereby standardizing the grip and improving the efficiency. When the flexible joint is inactive the accordion shaped metal sheet is open and the long axis of the bur lies perpendicular to the long axis of the index finger.

The FIG. 3(b) shows the perspective view of angle rotation of the dental hand piece device (300b). It shows the mechanism by which the head portion (320) of the hand piece is controlled by the distal-phalangeal joint. It shows the position of the head and the distal phalanx (312) when the flexible joint (340) is active. The accordion shaped metal sheet is then closed and the long axis of the bur is at an angle θ to the imaginary line perpendicular to the long axis finger. It can be seen that the movable joint closes when the finger bends at the distal-phalangeal joint (345). However, the proximal-phalangeal joint (350) may remain static as per the requirement.

FIGS. 4 (a) and 4 (b) shows the top view of head of dental hand piece and the finger facing depression surface of the hand piece according to one embodiment of the present invention.

The FIG. 4(a) shows the top view of head portion of dental hand piece device (400a). The body portion (410) is so designed that it provides two depressions (402) on both the lateral sides of the distal end, for resting the thumb (406) and the middle finger (404). This design provides a standard grasp of the hand piece to be used by different operators. The contra-angulation, lateral depressions (402) and flexible joint of the dental hand piece device aids in reaching the areas in the mouth which are difficult to access with much ease and with better control over the device, when compared to the normal available hand pieces which are less flexible.

The present device easily reaches the less accessible carious areas in the oral cavity and cuts the specific desired area and preserves the natural tooth to a greater extent, thus prompting Minimal Intervention Dentistry.

The FIG. 4(b) shows a closer view of the seating of the phalanges in the depressions (400b) present on the lateral aspects of the instrument. It shows attachment of the lateral aspect of the hand piece and the fingers.

Figure 5A:
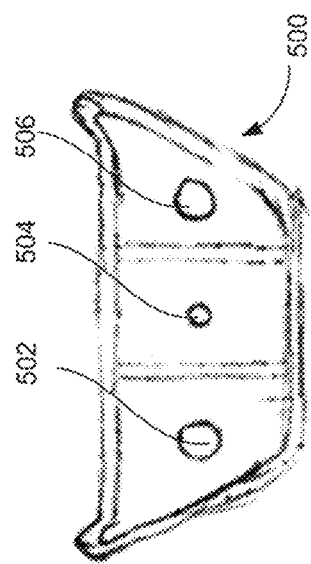
FIG. 5 (a) shows the cross section view of the body of the dental hand piece device according to one embodiment of the present invention.
FIG. 5(b) shows the cross section view of the mid part compartments of the body portion of dental hand piece device according to one embodiment of the present invention.
Figure 5B:
Figure 5C:
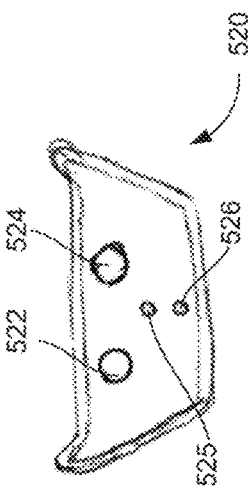

FIG. 5 (a) shows the cross section view of end part compartments of the body portion of dental hand piece device according to one embodiment of the present invention.

The figure shows the cross section view of end part compartments of body portion (500a) of dental hand piece. The inner hollow space of the body portion consists of three or more compartments each with a metal pipe, where the first (502) and the third/last (506) compartments have metal pipes for air inlet and air exhaust while the second/middle (504) one consists of a metal pipe for water inlet.

The compartmentalisation has been done so that the three metal pipes do not come in contact with each other which increases the efficiency and reduces the possible interlocking of the serrations present on the outer surface of the metal pipes, when the joint is active. Due to the presence of the compartments, each of the metal pipes will have a separate pathway in which the pipe can move freely.

FIG. 5(b) shows the cross section view of the mid part compartments of the body portion of dental hand piece according to one embodiment of the present invention.

The figure shows the cross section view of the mid part compartments (510) of body portion of dental hand piece at the level close to the flexible joint or hinge point. The three or more compartments of the body portion of hand piece dissolve and exist as a single compartment at this level.

FIG. 5 (c) shows the cross section view of end part compartments of body portion of dental hand piece according to one embodiment of the present invention.

The figure shows the cross section view of end part compartments (520) of body portion close to the head portion of dental hand piece. The body portion and the head portion of the dental hand piece are joined by fusing/welding.

The two sideway (522, 524) compartments positioned in the body portion of hand piece are for air inlet and air exhaust. In the core of sideway compartments, there are extension inlets (525, 526) with smaller diameter positioned vertically. The first extension inlet (525) is for the air inlet and the second extension inlet (526) is for water inlet. Both the extension inlets operate together as the coolant.

FIG. 6(a) shows the longitudinal section view of the dental hand piece device with the flexible joint inactive according to one embodiment of the present invention.

The figure shows longitudinal section view of the body portion of the dental hand piece (600) having a plurality of compartments with metal pipe/tubes (not shown) in the inner hollow space of the body portion of hand piece. As an example, the figure shows one of the compartments with metal pipe in the hollow space of the body portion. The hand piece device has a peripheral metal covering (602, 606) in the summit and base of body portion which is a metal structure providing the outer covering, circumscribing the body and includes the hinge point (612) in the superior/summit aspect at the centre or the ¾ portion of peripheral metal covering (602) of body portion providing flexible movement to the head portion of dental hand piece (600). The inner hollow space (604) in the body portion with metal pipes or tubes for water inlet, air inlet or air exhaust, depends on the compartment that lies at the level at which the section is made as shown in fig.

Further the figure shows the flexible joint in an inactive position in the body portion of dental hand piece. The dental hand piece device is finger mounted with size adjustable finger rings comfortable for all finger sizes. It is provided with a hinge point at the ¾th area of peripheral metal covering of the dental hand piece device which may be controlled by the distal inter-phalangeal joint of the index finger. Thus, the finger and the shortened dental hand piece work as a single unit to reach the less accessible areas of the oral cavity easily with the assistance of finger band/ring on the head and body portion of the dental hand piece device.

The inner hollow space where the various inlets and exhaust lie, is just enough to accommodate one pipe or tube of required diameter except for the reservoir, where the space is in slight excess. This reservoir sector (608) lies in the core of the inner hollow space of body portion of the dental hand piece device. The pipe or tube (608) in the inner hollow space in the body portion bends slightly in the reservoir sector, which is straight elsewhere, so as to accommodate slightly more length of the tube or pipe in the enclosing.

FIG. 6(b) shows the longitudinal section view of the dental hand piece device with the flexible joint activated according to one embodiment of the present invention.

The figure shows longitudinal section view of the dental hand piece device (620) when the flexible joint/hinge point (622) is active. The pipe or tube (624), as shown in the figure, lying in the reservoir sector straightens when the dental hand piece is stretched or bent to work in the less accessible areas in the oral cavity of the patient. The same mechanism is applied to other pipes or tubes (624) (not shown in figure). This extra length accommodated in the reservoir prevents the pipe or tube from getting compressed at the point of the bend preventing any hindrance that may occur in the streamline flow of air and water due to bending of the pipe/tube.

FIG. 6(*c*) shows the body configuration of the pipe or tube and its attachment to the slot in the head of the dental hand piece device (630) according to one embodiment of the present invention.

The figure shows the configuration of the pipe or the tube and its attachment to the slot (632) which protrudes from the enclosing which encloses the turbine (not shown). The figure shows the cross section view of the end part of body portion and the head portion of the dental hand piece. The outer housing of the body is designed in such a way that it fits the index finger on the superior aspect while having a flat interior surface. The body portion with plurality of compartments interiorly engages to the head portion with the assistance of a metal slot (632) present in the head portion and a polysilicon elastomeric rubber pipe (634) in the body portion. The polysilicon elastomeric rubber pipe (634) is then covered with a solid flexible metal pipe with minimum spacing between them, which is then welded/bonded to the enclosing which encloses the turbine around the metal slot (632).

The solid flexible metal pipe (636) over the polysilicon elastomeric rubber pipe (634) prevents its dislodgement from the metal slot (632) on continuous use. If the solid flexible metal pipe covering is used alone without the polysilicon elastomeric rubber pipe (634), the striations present in the inner surface of the flexible metal pipe may hinder the streamline flow of water and air inside it and may affect the performance of the air turbine.

Raw materials to manufacture the dental hand piece device includes a metal block, solid flexible metal pipes, Air turbine, Copper wires, Poly-silicone base material.

Advantages of the Invention

Flexibility:
The movable joint in the device controlled by the index finger allows desired movements of the hand piece within the oral cavity, unlike the conventional rigid hand pieces.

Accessibility:
The contra-angulation and the flexible joint of the device aids in reaching the less accessible areas of the mouth with much ease and with better control over the device, when compared to the normal available hand pieces which are less flexible.

Tactile Sensitivity:
The firm attachment of the device with the finger increases the tactile sensitivity and helps to differentiate between soft carious lesion and hard dentin, as well as infected and affected dentin.

Ease of Use:
The unique model of attachment of the device which is to be mounted on the finger prevents unnecessary slipping of the device that can otherwise be experienced with the conventional air-rotor, which may cause intra oral injuries.

In special cases like periodontitis, AUNG etc., the proposed design is more efficient than the conventional dental hand pieces available.

A dental hand piece comprises of a cutting unit called Dental unit which is fit on a rotor turbine to be rotated at a speed of 2,000,000 rpm.

The present dental hand piece device is used for periodontitis patients with grade 1 or grade 2 mobility.

The invention is aimed to provide flexibility in the hand piece for better ergonomics and control to access difficult areas of the mouth and surfaces of teeth with ease. It also provides a design which allows the use of tactile sensitivity to distinguish between sound and decayed dentin so as to prevent excess cutting of tooth structure.

FIGS. 1-6 are merely for representation and are not drawn to scale. Certain portions thereof may be exaggerated, while others may be minimized. FIGS. 1-6 illustrate various embodiments of the invention that can be understood and appropriately carried out by those of ordinary skill in the art. In the above detailed description of embodiments of the invention, various features are grouped together in a single embodiment for the purpose of streamlining the disclosure. This device, unit or arrangement of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus, the following claims are hereby incorporated into the detailed description of embodiments of the invention, with each claim standing on its own as a separate embodiment.

It is understood that the above description is intended to be illustrative, and not restrictive. It is intended to cover all alternatives, modifications and equivalents as may be included within the spirit and scope of the invention as defined in the appended claims. Many other embodiments will be apparent to those skilled in the art upon reviewing the above description. The scope of the invention should, therefore, be determined with reference to the appended claims, along with the full scope of equivalents to which such claims are entitled. In the appended claims, the terms "including" and "in which" are used as plain-English equivalents of the terms "comprising" and "wherein," respectively.

We claim:

1. A finger mountable dental hand piece device, comprising:
   a head portion and a body portion, wherein the head portion and the body portion are engaged by a flexible joint to provide flexible movement for the head portion, wherein the flexible joint is a hinge joint in the body portion;
   the head portion defines a head enclosed in a head shell, accompanied by a first finger band which is stipulated on a top of the head shell; and
   the body portion has a first end and a second end, the first end is to engage with the head portion, wherein the body portion has a second finger band stipulated on a top of the body portion, wherein the body portion comprises of at least three compartments, a first compartment including an air inlet pipe, a second compartment including a water inlet pipe, and a third compartment including an air exhaust pipe, wherein the body portion further delineates a reservoir sector for accommodating an extra length of the air inlet pipe, the water inlet pipe, and the air exhaust pipe, wherein the extra length of the air inlet pipe, the water inlet pipe, and the air exhaust pipe is accommodated by bending the air inlet pipe, the water inlet pipe, and the air exhaust pipe in the reservoir sector, wherein the reservoir sector facilitates bending movement of the air inlet pipe, the water inlet pipe, and the air exhaust pipe without hammering a streamline flow of air and water in the air inlet pipe, the water inlet pipe, and the air exhaust pipe, and wherein the air inlet pipe, the water inlet pipe, and the air exhaust pipe, domiciled in the reservoir sector, straighten when the head portion is stretched.

2. The finger mountable dental hand piece device of claim 1, wherein the first finger band is configured to a distal phalanx of an index finger and the second finger band is configured to a middle phalanx of the index finger.

3. The finger mountable dental hand piece device of claim 1, wherein the first end of the body portion adaptively engages to the head portion with the assistance of a metal slot in the head portion and a rubber pipe in the body portion and the second end extends from the first end.

4. The finger mountable dental hand piece device of claim 1, wherein the body portion has two depressions on lateral sides for resting distal phalanges of a thumb and a middle finger.

\* \* \* \* \*